United States Patent [19]

Lin et al.

[11] Patent Number: 5,057,644
[45] Date of Patent: Oct. 15, 1991

[54] PROCESS FOR THE PURIFICATION OF ALPHA OLEFINS

[75] Inventors: Jiang-Jen Lin; Randall T. De Pue; Keith M. Kreitman, all of Houston, Tex.

[73] Assignee: Shell Oil Company, Houston, Tex.

[21] Appl. No.: 606,372

[22] Filed: Oct. 31, 1990

[51] Int. Cl.$^5$ .............. C07C 7/152; C07C 7/00; C07C 6/00
[52] U.S. Cl. ................... 585/850; 585/851; 585/852; 585/854; 585/855; 585/864; 585/645; 585/646; 585/647
[58] Field of Search .............. 585/850, 851, 852, 854, 585/855, 864, 645, 646, 647

[56] References Cited

U.S. PATENT DOCUMENTS

| | | | |
|---|---|---|---|
| 3,367,987 | 2/1968 | Walsh | 585/850 |
| 3,439,057 | 4/1969 | Calderon | 585/318 |
| 3,558,518 | 1/1971 | Zuech | 252/429 |
| 3,636,126 | 1/1972 | Menapace et al. | 585/314 |
| 3,647,906 | 3/1972 | Farley | 585/314 |
| 3,647,908 | 3/1972 | Medema et al. | 585/314 |
| 3,652,704 | 3/1972 | Eades et al. | 585/314 |
| 3,671,462 | 6/1972 | O'Hare et al. | 252/429 A |
| 3,686,136 | 8/1972 | Doyle | 252/429 B |
| 3,723,563 | 3/1973 | Bradshaw | 585/314 |
| 3,829,523 | 8/1974 | Singleton | 585/314 |
| 3,832,417 | 8/1974 | Ruhle | 585/314 |
| 3,940,346 | 2/1976 | Zuech | 252/430 |
| 4,266,085 | 5/1981 | Kim et al. | 585/645 |

FOREIGN PATENT DOCUMENTS

| | | | |
|---|---|---|---|
| 49-45367 | 12/1974 | Japan | 585/851 |
| 49-45368 | 12/1974 | Japan | 585/851 |
| 59-125438 | 11/1984 | Japan . | |
| 60-083043 | 10/1985 | Japan . | |
| 6814835 | 10/1967 | Netherlands . | |
| 1264973 | 6/1982 | U.S.S.R. . | |
| 1251854 | 11/1971 | United Kingdom . | |
| 1252799 | 11/1971 | United Kingdom . | |
| 1284931 | 8/1972 | United Kingdom . | |

*Primary Examiner*—Anthony Mc Farlane
*Assistant Examiner*—Nhat Phan

[57] ABSTRACT

This invention relates to a process for the purification of an alpha olefinic feedstock contaminated with internal olefins which process comprises contacting said alpha olefinic feedstock with ethylene in the presence of a catalyst comprising an organoborane promoted alkali metal doped molybdenum and/or rhenium oxide supported on an inorganic oxide support.

20 Claims, No Drawings

PROCESS FOR THE PURIFICATION OF ALPHA OLEFINS

FIELD OF THE INVENTION

This invention relates to a process for the purification of alpha olefins which process comprises contacting an alpha olefinic feed contaminated with internal olefins with ethylene in the presence of a catalyst comprising an organoborane promoted alkali metal doped molybdenum and/or rhenium supported on an inorganic oxide support.

BACKGROUND OF THE INVENTION

In the present commercial petroleum refinery techniques, hydrocarbon streams are obtained which are quite complex and contain terminal or alpha olefins and internal olefins. The alpha olefins are far more valuable than the internal olefins. While most such streams contain predominantly alpha olefins, the olefin mixtures also contain undesired amounts of internal olefins. The use of conventional means for purifying alpha olefins such as, for example, distillation results in a decreased amount of internal olefin contaminants, but still leaves a relatively large amount of internal oldefins in the alpha olefin feed. Purification of of alpha olefins contaminated with internal olefins of the same carbon number is particularly difficult. Hence, a process whereby the alpha olefins are purified of internal olefin contaminants would be quite useful.

It is known from U.S. Pat. No. 3,647,906, issued Mar. 7, 1972, to produce alpha olefins by reacting internal olefins and ethylene (i.e., ethenolysis) with a $Re_2O_7$-on-alumina catalyst at 140° C. However, the purities or selectivities to alpha olefins were not reported. In U.S. Pat. No. 3,658,927, issued Apr. 25, 1972 and *Journal of Catalysis*, 7, 269-276 (1967), a heterogeneous molybdenum oxide catalyst at high temperature was used for ethenolysis. The reaction produced alpha olefin with either low conversion or low selectivity.

In addition, a variety of catalysts have been employed for conducting disproportionation (ethenolysis) type reactions, such as those disclosed in U.S. Pat. No. 3,340,322, issued Sept. 5, 1967; U.S. Pat. No. 3,637,892, issued Jan. 25, 1972; U.S. Pat. No. 3,760,026, issued Sept. 18, 1973; U.S. Pat. No. 3,792,108, issued Feb. 12, 1974; U.S. Pat. No. 3,872,180, issued Mar. 18, 1975; and British Patent Specification No. 1,128,091, published Mar. 16, 1966. Among the catalysts that have been developed for the reaction of olefins with ethylene include inorganic refractory materials containing molybdenum and/or tungsten oxide.

Several patents disclose the use of promoter to enhance the catalyst activity. Elemental metal promoters selected from the group consisting of barium, magnesium, tungsten, silicon, antimony, zinc, manganese and tin are disclosed in U.S. Pat. No. 4,568,788, issued Feb. 4, 1986, U.S. Pat. No. 4,522,936, issued June 11, 1985, U.S. Pat. No. 4,524,235, issued June 18, 1985 and U.S. Pat. No. 4,629,719, issued Dec. 16, 1986. In addition, organometallic compounds, such as aluminum and tin alkyls to promote solid catalysts including molybdenum and rhenium oxide for the disproportionation are disclosed in U.S. Pat. No. 4,454,368, issued June 12, 1984 and U.S. Pat. No. 3,829,523, issued Aug. 13, 1974.

It has been found that alpha olefins having internal contaminants can be purified by a process which comprises contacting the contaminated alpha olefin feed with an organoborane promoted catalyst comprising an alkali metal doped molybdenum and/or rhenium oxide supported on an inorganic oxide support. During the process, the contaminated olefin feed is reacted with ethylene in the presence of the catalyst. The alpha olefins present undergo degenerate metathesis (ethenolysts) and are thus unchanged, whereas the internal olefin contaminants are converted to alpha olefins having a lower carbon number. This chemical transformation of the internal olefin contaminants to alpha olefins results in high purity alpha olefins as well as minimizes potential side reaction, such as self-metathesis and double bond isomerization.

It is therefore an object of this invention to provide a process for the purification of alpha olefins containing internal olefin contaminants. It is further an object of this invention to convert the internal olefin contaminants in the alpha olefin feedstock to alpha olefins having lower carbon numbers. Another object is to provide a catalyst system adapted for high efficiency reaction and high selectivity to alpha olefin production from internal olefins and ethylene. The catalyst system is required to convert the internal olefin contaminants to alpha olefins without significant olefin isomerization and ethylene polymerizations.

The present invention is therefore directed to a method of purifying alpha olefins, particularly to a method of removing internal olefins from alpha olefins.

SUMMARY OF THE INVENTION

This present invention relates to a process for the purification of an alpha olefinic feedstock contaminated with internal olefins which process comprises contacting said alpha olefinic feedstock with ethylene in the presence of a catalyst comprising an organoborane promoted alkali metal doped molybdenum and/or rhenium oxide supported on an inorganic oxide support.

It has been found that the activity and selectivity of a catalyst can be improved by contacting the catalyst with an organoborane compound under conditions suitable for the organoborane compound to promote the activity of alkali metal doped molybdenum and rhenium oxides. The activity of the catalyst can be enhanced up to several orders of magnitude rate increase by the presence of organoborane, thus enabling the ethenolysis reaction to be carried out at ambient temperature with advantages of high reaction productivity and product selectivity.

DESCRIPTION OF THE PREFERRED EMBODIMENTS

In the process of the instant invention, the purification of alpha olefins by ethenolysis is accomplished by contacting an alpha olefinic feedstock contaminated with internal olefins with ethylene in the presence of a catalyst comprising an organoborane promoted alkali metal doped molybdenum and/or rhenium oxide supported on an inorganic oxide support.

Alpha olefinic feedstocks which are suitable for purification according to the instant invention are alpha olefin feedstocks comprising more than 50% by weight alpha olefins. Suitable alpha olefinic feedstocks are available commercially. Commercial production of olefins comprised largely of alpha-olefins is commonly accomplished by the oligomerization of ethylene using procedures well known to the art. Examples include the olefins marketed in the United States by Shell Chemical Company under the trademark Neodene, and by Ethyl Corporation as Ethyl Alpha-Olefins. Specific procedures for preparing suitable olefins from ethylene are described in U.S. Pat. Nos. 3,676,523, 3,686,351, 3,737,475, 3,825,615, and 4,020,121. A particularly useful group of olefin feed materials for the process of the instant invention are acyclic olefins having carbon numbers ranging from $C_4$ to about $C_{40}$, preferably from $C_4$ to about $C_{30}$.

The alpha olefinic feedstock suitable for purification in the instant invention will comprise alpha or terminal olefins and internal olefins. Among the alpha olefins included are, for example, 1-butene, 1-pentene, 1-hexene, 1-heptene, 1-octene, 1-nonene, 2-methyl-1-butene, 3-methyl-1-butene, 2-methyl-1-pentene, 3-methyl-1-pentene, 1-diisobutylene, 1-decene, 1-tetradecene, 1-octadecene, 1-dodecene, 1-hexadecene, styrene and the like. The internal olefins included are, for example, 2-butene, 2-pentene, 2-hexene, 3-hexene, 2-heptene, 2-nonene, 2-decene, 2-tetradecene, 2-methyl-2-butene, 2-methyl-2-pentene, 2-methylstyrene, 3-octene, 4-octadecene, cyclopentene, cyclohexene, cycloheptene, cyclooctene, cyclodecene, 1,2-diphenylethylene, and the like. In general, the olefins contained in the feedstock will contain up to about 40 carbon atoms. The process is especially applicable to mixtures containing olefins having up to about 18 carbon atoms and preferably up to about 12 carbon atoms. Particularly preferred olefin feedstocks are those containing any one or all of the following alpha olefins: 1-butene, 1-pentene, 1-hexene, 1-heptene, 1-octene, and 1-nonene and 1-decene and any or all of the following internal olefins: 2-butene, 2-pentene, 2-hexene, 3-hexene, 2-heptene, 3-heptene, 2-octene, 3-octene, 4-octene, 2-nonene, 3-nonene, 4-nonene, 2-decene, 3-decene, 4-decene and 5-decene.

The catalyst in the instant invention is prepared by forming a calcined composite comprising molybdenum and/or rhenium oxide and an alkali metal supported on an inorganic oxide support and contacting the calcined composite with a promoting amount of an organoborane compound. As used herein, "alkali metal" shall mean lithium, sodium, potassium, cesium and/or rubidium. The inorganic oxide support comprises a solid usually containing a major proportion of silica or alumina. Such materials are commonly known as refractory oxides and include synthetic products as well as acid-treated clays or the crystalline alumina silicates known in the art as molecular sieves. Synthetic refractory oxides include silica, alumina, silica-alumina, silica-magnesia, silica-titania, alumina-titania, alumina-magnesia, boria-alumina-silica, alumina-zirconia, thoria and silica-titania-zirconia. Preferred inorganic oxide supports are alumina refractory oxides, i.e., refractory oxides containing a substantial proportion of alumina, e.g., at least about 90 percent by weight of alumina. Any conventional catalytic grade of alumina including the beta or gamma forms can be used. Generally, the inorganic oxide support has a surface area of at least 10 $m^2/g$ and preferably, the surface area is from about 25 $m^2/g$ to 800 $m^2/g$.

The molybdenum and/or rhenium oxide can be combined with the inorganic oxide support in any conventional method such as dry mixing, ion-exchange, coprecipitation, impregantion and the like. For example, a 10–100 mesh alumina can be impregnated with an aqueous solution containing solubilized salts of molybdenum salts, such as ammonium heptamolybdate or ammonium dimolybdate, and alkali metal, such as alkali metal hydroxides, carbonates and oxides or compounds which decompose upon calcination to alkali metal oxidic compounds. The impregnation may be carried out in one step utilizing both metals dissolved in a solution or it may be carried out in a multi-step process using each of the metal salts dissolved in individual impregnating solutions, with the impregnation taking place sequentially. The impregnating steps may be repeated one or more times to provide the optimal metal loading.

In a preferred embodiment, the catalyst in the instant invention is a alkali metal doped molybdenum oxide prepared by impregnating alumina with an aqueous impregnation solution containing molybdenum salts and cesium salts. The aqueous impregnation solution consists of a water-soluble source of molybdenum oxide such as ammonium heptamolybdate or ammonium dimolybdate dissolved in water and a water-soluble source of alkali metal such as cesium nitrate or potassium nitrate. Hydrogen peroxide may also be used to aid in solution preparation in some cases. For example, the impregnation solution can be prepared by adding hydrogen peroxide to the solution in an amount in the range of from about 0.1 to about 1.0 mole of hydrogen peroxide per mole of molybdenum. Optionally, a suitable soluble amine compound such as monoethanolamine, propanolamine or ethylenediamine may be added to the impregnation solution in order to aid in stabilization of the solution.

Following impregnation, the resulting material is dried and calcined. Drying is accomplished by conventional means. It may be carried out by forced draft drying, vacuum drying, air drying or similar means. Drying temperatures are not critical and depend upon the particular means utilized for drying. Drying temperatures will typically range from about 50° C. to about 150° C.

After drying, the material is calcined to produce the finished catalyst. The material may be calcined in an oxidizing or neutral atmosphere, although air is preferred. However, if binders and/or lubricants are used the material is heated in an oxygen-containing atmosphere, preferably air, in order to burn out the binders and lubricants. Calcining temperatures will typically range from about 300° C. to about 600° C. Burn-out temperatures will depend on the concentration of oxygen in the burn-out atmosphere as well as the burn-out time involved. Typically, burn-out temperatures will range from about 300° C. to about 600° C. Drying, calcining and burn-out may be combined in one or two steps. Most frequently the calcining and/or burn-out steps are combined using an oxygen-containing atmosphere.

The final calcined composites typically contain from about 1 percent by weight to about 18 percent by weight, preferably from about 5 percent by weight to about 15 percent by weight, and more preferably from about 6 percent by weight to about 12 percent by weight molybdenum, and from about 1 percent by weight to about 20 percent by weight, preferably from about 5 percent by weight to about 15 percent by weight, and more preferably from about 6 percent to about 12 percent by weight rhenium. When mixtures of molybdenum and rhenium are utilized, the final catalyst typically contains from about 1 percent by weight to about 32 percent by weight molybdenum and/or rhenium. The amount of alkali metal dopent present in the final catalyst, measured as a metal will range from about 0.01 percent by weight to about 10 percent by weight, preferably from about 0.05 percent by weight to about 5 percent by weight and more preferably, from about 0.1 percent by weight to about 1 percent by weight.

The supported alkali metal doped molybdenum and/or rhenium oxide composites are preferably subjected to a pretreatment prior to contact with the organoborane compound. While pretreatment is usually accomplished by contacting the catalyst with an oxygen-containing gas at elevated temperatures, other activation methods such as heating under a vacuum, or contact with various gases such as nitrogen or argon at high temperatures, can be used. One function served by this type of pretreatment is to convert the alkali metal and the molybdenum and/or rhenium components into the form of the oxide if these components are not initially provided in these forms. The temperature, contact times, and other conditions of pretreatment have been reported in the prior art and are generally the same conditions which are utilized to activate a disproportionation-type catalyst. Typically, the pretreatment conditions include a temperature in the range of from about 300° C. to about 900° C. for about 30 minutes to about 24 hours.

In order to obtain a catalyst composition active for the purification of alpha olefins according to the process of the instant invention, the alkali metal doped molybdenum and/or rhenium oxide supported composition is treated with an organoborane compound. The promoting organoborane compound can be combined with the molybdenum or rhenium oxide supported compositions in any suitable manner. For example, the alkali metal doped molybdenum and/or rhenium oxide supported composition can be impregnated with a liquid diluent containing the organoborane compound at ambient temperature up to 150° C. After impregnation, the catalyst is then heated in an inert atmosphere, such as nitrogen or argon, to remove the liquid diluent. The temperature employed in removing the diluent and activating can vary widely; however, temperatures in the range of about 25° C. to about 200° C. are preferred. If desired, the promoter can be applied to the supported alkali metal doped molybdenum and/or rhenium oxide in a reaction zone by spraying or otherwise contacting with the oxide. It is also contemplated that the promoter can be introduced along with the olefin feed as a means for contacting with supported alkali metal doped molybdenum and/or rhenium oxide.

In accordance with the invention, the calcined alkali metal doped molybdenum and/or rhenium oxide refractory materials are treated with an effective promoting amount of an organoborane compound and heated under conditions to form a promoted catalyst. The organoborane promoter should have at least one boron to carbon bond. The preferred organoborane compounds are alkylboranes such as triethylborane, tri-sec-butylborane, tri-n-butylborane, trimethylborane, tricyclohexylborane and the like, with tri-sec-butylborane and triethylborane being preferred. Suitable molybdenum or rhenium oxide/organoborane molar ratios are typically in the range of from about 0.1 to about 50, preferably from about 1 to about 30 and more preferably, from about 1.5 to about 25.

The process of the invention can be carried out either batchwise or continuously, using a fixed catalyst bed, or a stirrer equipped reactor or other mobile catalyst contacting process as well as any other well known contacting technique. Preferred reaction conditions, e.g., temperature, pressure, flow rates, etc., vary somewhat depending upon the specific catalyst composition, the particular feed olefin, desired products, etc. The process is carried out at temperatures ranging from about −10° C. to about 350° C. and at pressure in the range of about 50 psig to about 2000 psig. The reaction is usually effected in a liquid phase and if desired, liquid reaction diluents are utilized. Examples of suitable diluents are hydrocarbons free from aliphatic unsaturation, such as cyclic or alicyclic alkanes of from 6 to 12 carbon atoms, i.e. hexane, isooctane and cyclohexane. Also exemplary would be monoaromatic compounds such as benzene and toluene. If the diluent is added, it is present in amounts up to 20 moles of diluent per mole of olefinic reactants.

The operable range of contact time for the process of this invention depends primarily upon the operating temperature and the activity of the catalyst, which is influenced by surface area, promoter concentration, activation temperature, etc. In general, the distribution of products is not drastically altered by variation in contact time. Shorter contact times are usually associated with higher temperatures. With proper selection of conditions and contact times, very high efficiency of conversion of the internal olefin contaminants to the desired alpha olefin products can be obtained.

With a fixed bed reactor, continuous flow operation at pressures in the range of about 50 psig to about 2000 psig, preferably about 100 psig to about 1000 psig, with catalysts having densities ranging from about 0.3 gram per cc to about 2.0 gram per cc and surface areas greater than about 100 m$^2$/g, and at temperatures in the range of about −10° C. to about 350° C., preferably at room temperature, weight hourly space velocities in the range of about 0.1 to about 10.0 parts by weight of olefinic hydrocarbon feed per part by weight of catalyst per hour are suitable. The space velocity is adjusted according to changes in density of feed due to change of pressure or temperature, and variation in reaction temperature and the activity of the catalyst.

In a preferred embodiment, alpha olefins can be purified at room temperature by the ethenolysis of a mixture of alpha and internal olefins with ethylene as described in the following reaction:

$$CH_3(CH_2)_nCH=CH_2 + \text{isomers} \xrightarrow{H_2C=CH_2} CH_3(CH_2)_mCH=CH_2 + CH_3(CH_2)_nCH=CH_2$$

wherein n=1 to 15 and m<n.

Alpha olefins purified according to the instant process are used to produce a number of useful products, including comonomers for high density polyethylene (HDPE), linear low density polyethylene (LLDPE), intermediates for synthetic lube oils and lube oil additives, surfactants, paper sizings and specialty chemicals.

The ranges and limitations provided in the instant specification and claims are those which are believed to particularly point out and distinctly claim the instant invention. It is, however, understood that other ranges and limitations that perform substantially the same function in substantially the same manner to obtain the same result are intended to be within the scope of the instant invention as defined by the instant specification and claims.

The process of the instant invention will be further described below by the following examples which are illustrative and which are not to be construed as limiting the invention.

ILLUSTRATIVE EMBODIMENTS

Catalyst Preparation

The catalysts utilized in the examples below were prepared using a conventional dry pore volume impregnation technique.

A 6% $MoO_3/Al_2O_3$ catalyst was prepared as follows. A solution suitable for impregnating 88 grams of calcined alumina support with a pore volume of 1.0 cm/g was prepared as follows. An impregnation solution was made by combining 7.4 grams of ammonium heptamolybdate, 2.9 grams of 30% hydrogen peroxide and 16.2 grams of deionized water or enough water to bring the solution to a total volume of 88 milliliters. After adding the entire solution to the alumina support in several small portions with intermediate agitations, the impregnated support was dried overnight at 150° C. and calcined in air for at least 2 hours at 550° C. and in nitrogen for at least 1 hour at 550° C.

A 0.5% K/6% $MoO_3/Al_2O_3$ catalyst was prepared as follow. A solution suitable for impregnating 40 grams of calcined 6% $MoO_3/Al_2O_3$ catalyst was prepared as follows. An impregnation solution was made by dissolving 0.35 grams of potassium carbonate in 56 grams of deionized water. The solution was then added to the 6% $MoO_3/Al_2O_3$ catalyst which was subsequently dried, calcined in air for at least 2 hours at 550° C. and then calcined in nitrogen for at least 1 hour at 550° C.

A 0.2% Cs/6% $MoO_3/Al_2O_3$ catalyst was prepared as follows. An impregnation solution suitable for impregnating 40 grams of calcined 6% $MoO_3/Al_2O_3$ catalyst was prepared by dissolving 0.15 grams of cesium nitrate in 56 grams of deionized water. The solution was then added to the 6% $MoO_3/Al_2O_3$ catalyst, dried, calcined in air for at least 2 hours at 550° C. and then calcined in nitrogen for at least one hour at 55° C.

A 0.5% Cs/6% $MoO_3/Al_2O_3$ catalyst was prepared in a similar way by using 0.37 grams of cesium nitrate as the cesium oxide precursor.

PURIFICATION OF ALPHA OLEFINS

EXAMPLE 1

Example 1 involving the purification of $C_{12}$ alpha olefins (commercially available from Shell Chemical Company as NEODENE ® 12 Alpha-olefins) (20 ccs) by ethenolysis was carried out in a 80 mL autoclave which was charged with 4.0 grams of catalyst and a magnetic stir bar. The catalyst was activated with a solution of the required amount of tri-sec-butylborane (0.229 g, 1.25 mmoles) to give a molybdenum oxide to tri-sec-butylborane molar ratio (mole Mo/B) of 1.3. The catalyst was then suspended in 20.0 ml of $C_{12}$ alpha-olefins. The borane solution was added to the catalyst either before or after pressurization with ethylene. The reaction was performed at ambient temperature (approximately 21°-25° C.) under continuous pressure of purified ethylene, which was supplied on demand.

As can be seen in Table I, the purity of the $C_{12}$ alpha-olefin improves from 96% to 96.9% after a one hour reaction at 24° C.

EXAMPLE 2-3

Example 2-3 were carried out in the same manner as Example 1, except that different alkali metal doped molybdenum oxide catalysts and a different tri-sec-butylborane molar ratios were used. The results are presented in Table I.

As can be seen in Table I, the purity of $C_{12}$ alpha-olefins improve from 96% to 97.8% for Example 2 and from 96% to 97.6% for Example 3.

COMPARATIVE EXAMPLE A

Comparative Example A was carried out in the same manner as Example 1 except that no alkali metal was present in the catalyst. The results of the ethenolysis reaction are presented in Table 1.

COMPARATIVE EXAMPLE B

Comparative Example B was carried out in the same manner as Example 2, except that no borane promoter was present. The results of the ethenolysis reaction are presented in Table I.

TABLE I

| ETHENOLYSIS OF $C_{12}$ ALPHA-OLEFIN AT 1300 PSI WITH ALKALI DOPED CATALYSTS | | | | | | | | | | | |
|---|---|---|---|---|---|---|---|---|---|---|---|
| Catalyst | | | Conditions | | Product Dist. | | | $C_{12}$ Compositions | | | |
| Wt % Alkali Metal | Wt % $MoO_3$ | Mole Mo/B | Temp °C. | Rxn Hrs | Weight % (Uncorr.) | | | Weight % (Uncorr.) | | | |
| | | | | | $C_{8-11}$ | $C_{12}$ | $C_{22}$ | AO | IO | Br | Unk |
| $C_{12}$ Alpha Olefin | | | | | 0.88 | 97.46 | 0.0 | 96.0 | 1.7 | 2.3 | 0.0 |
| Example 1 | 0.5% K | 6 | 1.3 | 25 | 0.25 | 1.42 | 97.01 | 0.16 | 96.5 | 1.8 | 1.8 | 0.0 |
| | | | | 24 | 1.0 | 1.66 | 96.43 | 0.70 | 96.9 | 1.4 | 1.7 | 0.0 |
| Example 2 | 0.2% Cs | 6 | 7.1 | 24 | 0.25 | 1.55 | 94.54 | 0.70 | 96.8 | 1.7 | 1.5 | 0.0 |
| | | | | 24 | 2.0 | 4.76 | 91.51 | 1.25 | 97.8 | 0.7 | 1.4 | 0.0 |
| Example 3 | 0.5% Cs | 6 | 7.5 | 24 | 0.25 | 1.55 | 95.91 | 0.39 | 96.7 | 1.7 | 1.6 | 0.0 |
| | | | | 21 | 2.0 | 3.07 | 93.82 | 1.52 | 97.6 | 0.8 | 1.6 | 0.0 |
| Comparative Example A | None | 6 | 4.7 | 21 | 0.5 | 2.99 | 94.34 | 0.93 | 96.6 | 1.5 | 1.6 | 0.3 |
| | | | | 22 | 2.0 | 5.47 | 90.47 | 1.25 | 97.0 | 1.0 | 1.7 | 0.3 |
| Comparative Example B | 0.2% Cs | 6 | No Borane | 25 | 0.5 | 0.50 | 99.40 | — | 93.6 | 4.9 | 1.5 | — |
| | | | | 25 | 2.0 | 0.60 | 99.30 | — | 92.5 | 5.6 | 1.9 | — |

I claim as my invention:

1. A process for the purification of an alpha olefinic feedstock contaminated with internal olefins which process comprises contacting said alpha olefinic feedstock with ethylene in the presence of a catalyst comprising an organoborane promoted, alkali-metal doped molybdenum oxide and/or rhenium oxide supported on an inorganic oxide support.

2. The process of claim 1 wherein said organoborane is selected from the group consisting of triethylborane, tri-sec-butylborane, tricyclohexylborane, 9-borabicyclo[3,3,1]nonane, diethylborane and mixtures thereof.

3. The process of claim 2 wherein said organoborane is selected from triethylborane and tri-sec-butylborane.

4. The process of claim 1 wherein the molybdenum and/or rhenium/organoborane molar ratio is in the range of from about 0.1 to about 50.

5. The process of claim 4 wherein the molybdenum and/or rhenium/organoborane molar ratio is in the range of from about 1 to about 30.

6. The process of claim 5 wherein the molybdenum and/or rhenium/organoborane molar ratio is in the range of from about 1.5 to about 25.

7. The process of claim 1 wherein said alkali metal is selected from the group consisting of lithium, sodium, potassium, cesium, rubidium and mixtures thereof.

8. The process of claim 7 wherein said alkali metal is selected from potassium and cesium.

9. The process of claim 7 or 8 wherein said catalyst contains from about 0.05 percent by weight to about 5 percent by weight alkali metal.

10. The process of claim 9 wherein said catalyst contains from about 0.1 percent by weight to about 1 percent by weight alkali metal.

11. The process of claim 1 wherein said catalyst contains from about 1 percent by weight to about 18 percent by weight molybdenum.

12. The process of claim 11 wherein said catalyst contains from about 5 percent by weight to about 15 percent by weight molybdenum.

13. The process of claim 12 wherein said disproportionation catalyst contains from about 6 percent by weight to about 12 percent by weight molybdenum.

14. The process of claim 1 wherein said catalyst contains from about 1 percent by weight to about 20 percent by weight rhenium.

15. The process of claim 14 wherein said catalyst contains from about 5 percent by weight to about 15 percent by weight rhenium.

16. The process of claim 15 wherein said catalyst contains from about 6 percent by weight to about 12 percent by weight rhenium.

17. The process of claim 1 wherein said inorganic oxide support is selected from the group consisting of silica, alumina, silica-alumina, silica-magnesia, silica-titania, alumina-titania, alumina-magnesia, boria-alumina-silica, alumina-zirconia, thoria, silica-titania-zirconia and mixture thereof.

18. The process of claim 17 wherein said inorganic oxide support is alumina.

19. The process of claim 1 wherein said alpha olefinic feedstock containing internal olefin contaminants has carbon numbers ranging from $C_4$ to about $C_{40}$ and contains more than about 50 percent by weight alpha olefins.

20. The process of claim 1 wherein said process is carried out at a temperature in the range of from about $-10°$ C. to about $350°$ C. and a pressure in the range of from about 50 psig to about 2000 psig.

* * * * *